(12) United States Patent
Derks

(10) Patent No.: US 8,268,298 B2
(45) Date of Patent: Sep. 18, 2012

(54) COSMETIC OR PERSONAL CARE COMPOSITION COMPRISING A POLYMER COMPRISING OXAZOLIDON GROUPS

(75) Inventor: Franciscus Johannes Marie Derks, Heythuysen (NL)

(73) Assignee: DSM IP Assets B.V., Heerlen (NL)

(*) Notice: Subject to any disclaimer, the term of this patent is extended or adjusted under 35 U.S.C. 154(b) by 0 days.

(21) Appl. No.: 13/183,302

(22) Filed: Jul. 14, 2011

(65) Prior Publication Data

US 2011/0268685 A1    Nov. 3, 2011

Related U.S. Application Data

(62) Division of application No. 12/089,477, filed as application No. PCT/EP2006/011359 on Nov. 27, 2006, now abandoned.

(30) Foreign Application Priority Data

Nov. 25, 2005    (EP) ..................................... 05077672

(51) Int. Cl.
*A61Q 5/00* (2006.01)
(52) U.S. Cl. ...................................... 424/70.11; 424/47
(58) Field of Classification Search .................. None
See application file for complete search history.

(56) References Cited

U.S. PATENT DOCUMENTS

| | | | |
|---|---|---|---|
| 3,480,557 A | 11/1969 | Shiraeff et al. | |
| 4,463,143 A | 7/1984 | Holubka | |
| 4,658,007 A | 4/1987 | Marks et al. | |
| 5,112,932 A | 5/1992 | Koenig et al. | |
| 5,272,189 A | 12/1993 | Kaufman | |
| 5,276,072 A | 1/1994 | Ishii et al. | |
| 5,320,738 A | 6/1994 | Kaufman | |
| 5,446,077 A | 8/1995 | Yamada et al. | |
| 5,447,973 A | 9/1995 | Yamada et al. | |
| 5,536,804 A | 7/1996 | Yamada et al. | |
| 5,770,642 A | 6/1998 | Kanato et al. | |
| 6,432,541 B1 | 8/2002 | Gan | |

FOREIGN PATENT DOCUMENTS

| | | |
|---|---|---|
| EP | 1 529 462 | 5/2005 |
| JP | 2000-128959 | 5/2000 |
| JP | 2005-306327 | 11/2005 |
| JP | 2006-329755 | 12/2006 |
| WO | WO 86/06734 | 11/1986 |
| WO | WO 00/34351 | 6/2000 |
| WO | WO 2005/005510 | 1/2005 |

OTHER PUBLICATIONS

International Search Report for International Application No. PCT/EP2006/011359, mailed Mar. 20, 2007.
Written Opinion of the International Searching Authority, mailed Mar. 20, 2007.

*Primary Examiner* — Jyothsna Venkat
(74) *Attorney, Agent, or Firm* — Nixon & Vanderhye P.C.

(57) ABSTRACT

The invention relates to a cosmetic or personal care composition comprising a polymer which polymer comprises oxazolidon groups. Examples of cosmetic and personal care compositions include hair spray compositions, mousses, gels, lotions, tonics, shampoos, conditioners, rinses, hand and body lotions, facial moisturizers, sunscreens, anti-acne preparations, topical analgesics, mascara's, eyeliners, blush, liquid lip color, nail polish foundations.

9 Claims, No Drawings

COSMETIC OR PERSONAL CARE COMPOSITION COMPRISING A POLYMER COMPRISING OXAZOLIDON GROUPS

This application is a divisional of commonly owned U.S. application Ser. No. 12/089,477, filed Mar. 7, 2008, now abandoned which is the national phase application under 35 USC §371 of PCT/EP2006/011359, filed Nov. 27, 2006 which designated the US and claims benefit of EP 05077672.3, filed Nov. 25, 2005, the entire contents of each of which are hereby incorporated by reference.

The invention relates to a cosmetic or personal care composition comprising a polymer which polymer comprises oxazolidon groups.

Examples of cosmetic and personal care compositions include hair spray compositions, mousses, gels, lotions, tonics, shampoos, conditioners, rinses, hand and body lotions, facial moisturizers, sunscreens, anti-acne preparations, topical analgesics, mascara's, eyeliners, blush, liquid lip color, nail polish and foundations.

A hair care product for example must meet a variety of requirements including exhibiting find spray pattern, good film formation, good holding power, prolonged curl retention, low stickiness, lack of powdering or flaking, being clear, transparent and glossy and easy to remove upon washing the hair with shampoo or soap. Lately it has become especially desirable to provide a high level of style retention, or strong hold, from a hair care product.

In a typical hair care composition hold is achieved by the use of polymers, also indicated by hair styling polymers. Examples of known hair styling polymers are for example given in U.S. Pat. No. 6,730,289 and include copolymers of vinyl acetate and crotonic acid, copolymers of methyl vinyl ether and maleic anhydride, copolymers of acrylic acid or metacrylic acid with other monomers, polyurethanes, N-vinylpirrolidone and silicone polymers.

Also in other cosmetic compositions the use of polymers is becoming more and more important, for example to improve rheological behaviour or adhesion to skin, nails etc.

There is a need for further polymers suitable for use in cosmetic compositions, such as for example hair styling polymers.

Surprisingly polymers suitable for use in cosmetic compositions are polymers comprising oxazolidon groups in the main chain of the polymer. Such compositions show a good balance of properties, especially a high level of style retention is obtained as styling polymer in hair care compositions. The polymers comprising oxazolidon groups in the main chain show a good adhesion to skin and hair.

The polymers comprising oxazolidon groups in the main chain are also suitable to be used as film formers in mascara, lip color, nail polish etc.

The oxazolidon groups may further be present as side groups or in the side chains of the polymer.

The oxazolidon group is suitably formed by the reaction of an epoxide and an isocyanate group.

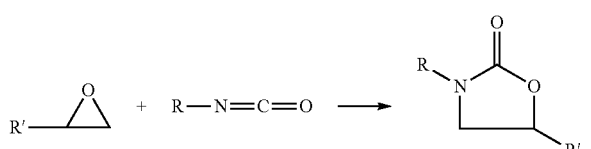

Such a polymer may suitably be formed from a reaction mixture comprising at least one epoxide functional compound and at least one isocyanate functional compound.

The epoxide functional compound may contain one or more of epoxy, i.e. α,β-oxirane groups. It is preferred that the functionality of the epoxide functional compound is from 2 to 10, more preferably 2 to 4, and most preferably 2 to 3. Lower functionalities are preferred because they give rise to less highly branched polymers. Preferably diepoxides are used, which give rise to linear polymers when reacted with a diisocyanate.

Monoepoxides may be used as chain stoppers.

Among the polyepoxides usefully employed herein are those represented by the general structure

(I)

wherein X is the residue of an active hydrogen-containing moiety after removal of said active hydrogen, R' is an organic mono- or polyradical and n is at least 1. n is preferably from 2 to 4 more preferably from 2 to 3. Such epoxide functional compounds are advantageously prepared by reacting a compound having a plurality of groups containing active hydrogen atoms with a halogen-containing oxirane such as epichlorohydrin or epibromohydrin.

In structure I, the group X is advantageously —O—, —NH—,

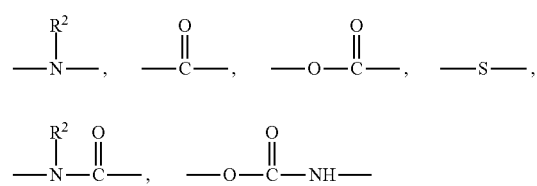

or a similar group, wherein $R^2$ is inertly substituted lower alkyl or phenyl. Preferably, the group X is —O— and the epoxide functional compound is one prepared in the reaction of a polyhydroxyl containing compound with a halogenated oxirane as discussed hereinbefore.

Specific examples of compounds according to structure I include epoxy terminated polyethylene glycol, epoxy terminated polypropylene glycol and epoxy terminated polytetrahydrofuran. Further suitable examples include diepoxides resulting from the reaction between epichorohydrin and ethylene glycole, diethylene glycol, neopentylglycol, respectively butane diol.

Further epoxide functional compounds include epoxy-terminated derivatives of bisphenols, such as are represented by the structure (II)

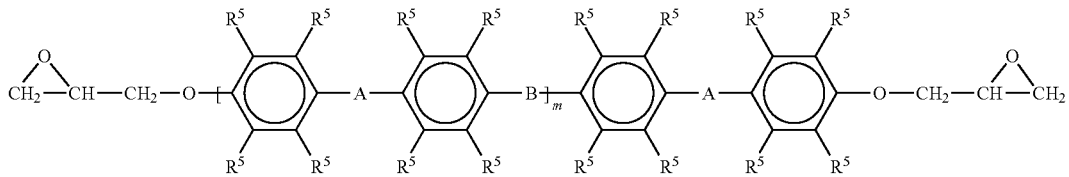

(II)

herein each A is independently a lower alkylene group such as methylene, ethylene, isopropylidine and the like, —O—, —S—, $$-\overset{O}{\underset{\|}{C}}-$$

and the like, each B is as defined by A, and/or —OCH$_2$CHOHCH$_2$O—, each R$_5$ is independently hydrogen, halogen or lower alkyl, and m is a number from 0 to 30, preferably 0 to 10 and more preferably 0.1 to 3. In addition, derivatives of the materials represented by structure (II) in which one or more of the positions on the group A is substituted with an inert substituent such as halogen, aryl, alkyl and the like are also useful herein. Suitable such epoxies include the commercially available resinous reaction products of an epihalohydrin with the diverse bisphenols and halogenated bisphenols, particularly the reaction products of an epihalohydrin with bisphenol A or bisphenol F or halogenated derivatives thereof.

Also suitable are the corresponding aromatic glycidyl amine resins wherein the various ether linkages are replaced by —NH— groups.

Also suitable are the so-called epoxy phenol novolac resins and epoxy cresol novolac resins which can be represented by the structure (III)

cyanate, hydrogenated xylene diisocyanate, hexamethylene-1,6-diisocyanate, cyclohexane-1,4-diisocyanate, hexahydrotolylene diisocyanate (and isomers), naphthalene-1,5-diisocyanate, 1-methoxyphenyl-2,4-diisocyanate, diphenylmethane-4,4'-diisocyanate, 4,4'-biphenylene diisocyanate, 3,3'-dimethoxy-4,4'-biphenyl diisocyanate, and 3,3'-dimethyl-4,4'-diphenyl diisocyanate, the triisocyanates such as trifunctional polymethylene polyphenylisocyanates and tolylene-2,4,6-triisocyanate; and tetraisocyanates such as 4,4'-dimethyldiphenylmethane-2,2',5,5'-tetraisocyanate and the like.

Most preferred isocyanates are tolylene-2,4-diisocyanate, tolylene-2,6-diisocyanate, isophorone diisocyanate, diphenyl methane diisocyanate, hydrogenated diphenyl methane diisocyanate, hexamethylene-1,6-diisocyanate.

A suitable process for the formation of oxazolidon groups is disclosed in U.S. Pat. No. 4,658,007. Herein a process is disclosed wherein an epoxy functional compound and an isocyanate functional compound are reacted in the presence of an organo-antimony iodide catalyst. In general a reaction temperature between 80 and 180° C. is suitable. Also other catalysts such as secondary and tertiary amines, halide salts of amines, carboxylate anions, zinc chloride, ferric chloride, lithium chloride, lithium bromide or its complex with tributyl phosphineoxide can be used.

The reaction may be carried out neat, but may also be carried out in the presence of a solvent.

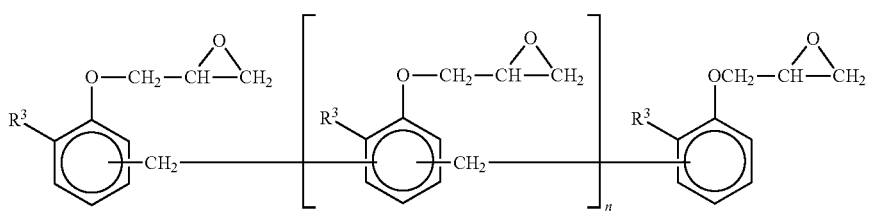

(III)

wherein n is for example a number from 0-20 and each R$_3$ is independently hydrogen, halogen, lower alkyl, aryl or aralkyl.

Also useful are aliphatic epoxy resins prepared in reaction of cycloolefins with peracetic acid, as well as diglycidyl ethers of cyclic dicarboxylic acids.

As isocyanate functional compounds preferably polyisocyanates, most preferably diisocyanates are used. Polyisocyanates which may be employed include aromatic, aliphatic and cycloaliphatic polyisocyanates and combinations thereof.

Representative of these types are diisocyanates such as m-phenylene diisocyanate, tolylene-2,4-diisocyanate, tolylene-2,6-diisocyanate, xylenediisocyanate, tetramethylxylene diisocyanate, isophorone diisocyanate, diphenyl methane diisocyanate, hydrogenated diphenyl methane diiso- The relative proportions of the epoxy functional compound or the isocyanate functional compound employed, will control to a large extend the characteristics of the resulting oxazolidon polymer. Either the epoxy functional compound or the isocyanate functional compound can be used in excess. The use of an excess of an epoxy functional compound will result in the formation of epoxide terminated oxazolidon polymers. The use of an excess of an isocyanate functional compound will result in the formation of isocyanate terminated oxazolidon polymers. The molecular weight of the oxazolidon group comprising polymer will among other factors be determined by the epoxy:isocyante ratio. The number average molecular weight may be between 500 and 1,000,000, preferably between 1000 and 100,000 and most preferably between 1000 and 20,000.

It is possible that the oxazolidon group comprising polymer further comprises compounds to be incorporated in the oxazolidon group-comprising polymer, for example hydroxyl functional compounds and/or amine functional compounds. Preferably the oxazolidon group comprising polymer further comprises at least one hydroxyl functional compound and/or at least one amine functional compound. However, preferably the polymer is formed in a process wherein in the first step the epoxy functional compound and the isocyanate functional compound are reacted to form a polyoxazolidon group containing polymer precursor and wherein in one or more further steps the polymer precursor is reacted with at least one of the further compounds, preferably at least one hydroxyl functional compound and or at least one amine functional compound. In this way the reaction condition for the formation of the oxazolidon groups can be better adapted.

In case that in the first step isocyanate terminated oxazolidon group comprising polymers are formed, it is possible to use hydroxyl and/or amine functional compounds as the further compounds. In case that epoxy terminated oxazolidon group comprising polymers are formed it is very well possible to use amine functional compounds as the further compounds.

As the hydroxyl functional compounds monomeric or polymeric alcohols, diols or polyols may be used.

Examples of monomeric alcohols include n-alkyl alcohols like methanol, ethanol propanol etc. Examples of polymeric alcohols include monomethoxy polyethylene glycol, monomethoxy polypropyleneglycol. Examples of monomeric diols include ethylene glycol, diethylene glycol, triethylene glycol, propylene glycol, dipropylene glycol, propanediol, butanediol, neopentyl glycol, cyclohexanediol, cyclohexanedimethylol, bisfenol A, hydrogenated bisfenol A. Examples of polymeric dials include polyethylene gycol, polypropylene gycol, polytetrahydrofuran, polymethyl tetrahydrofuran, polybutadiene diol, hydrogenated polybutadiene diol, polyacrylate diol, aromatic or aliphatic polyester diol, ethoxylated bisfenol A at which de degree of ethoxylation is between 2 and 40, hydrogenated ethoxylated bisfenol A, polysiloxane diol and polycarbonate diol. Examples of monomeric polyols include trimethylol propane, trimethylol ethane, pentaerithritol. Examples of polymeric poyols include poly hydroxyl functional polyesters, polyacrylates, polysiloxanes.

As the amine functional compounds monomeric or polymeric monoamine, diamine and polyamine compounds may be used. The amines may be primary or secondary amines.

Examples include ethylamine, diethylamine, triethylamine, butane diamine, hexane diamine, isophorone diamine, amine functional polyethers, amine functional polytetrahydrofuran, amine functional polysiloxane.

Further examples of hydroxy functional and amine functional compounds are disclosed in EP-A-938.889.

Preferred hydroxy functional compounds include amino alcohols. This is because these compounds provide improved water compatibility or solubility. Examples of suitable amino alcohols are 2-aminoethanol, 2-(N-methylamino) ethanol, 3-aminopropanol, 4-aminobutanol, 1-ethylaminobutan-2-ol, 2-amino-2-methyl-1-propanol, 4-methyl-4-aminopentan-2-ol etc.

Also preferred hydroxy or amine functional compounds include compounds having at least one iogenic or ionic group per molecule, for example dimethyl di(2-hydroxyethyl)ammonium chloride or diethyl di(2-hydroxyethyl)ammonium chloride. More preferred hydroxy or amine functional compounds include compounds having at least one aniogenic or anionic group per molecule, for example compounds having carboxylate and/or sulfonate groups. This is because these compounds provide even further improved water compatibility or solubility. Particular preference is given to dimethylolpropanoic acid and mixtures comprising it.

It is also possible to use compounds of the formulae (A and/or B)

$$H_2N(CH_2)_n-NH-(CH_2)_m-COO^-M^+ \quad (A)$$

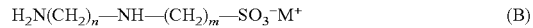

$$H_2N(CH_2)_n-NH-(CH_2)_m-SO_3^-M^+ \quad (B)$$

where m and n independently of one another are an integer from 1 to 8, in particular from 1 to 6, and M is Li, Na or K.

Further suitable compounds having an iogenic or ionic group are disclosed in U.S. Pat. No. 6,579,517. Also nitrogen containing compounds are suitable, for instance N—(C1-C6 alkyl)diethanol amines, such as for example methyl diethanol amine.

If compounds having nitrogen-containing compounds are used, cationic polymers may be obtained. These polymers are very suitable to be used in hair conditioners.

In principle suitable polymers are the polymers, used in cosmetic applications and comprising urethane groups, in which polymers at least an oxazolidon group has replaced a part of the urethane groups.

The invention therefore also relates to a polymer comprising the reaction product of an isocyanate functional oxazolidon polymer and an amino alcohol. The invention also relates to a polymer comprising an oxazolidon group and a residue of an hydroxy and/or amino functional compound having at least one iogenic or ionic group per molecule preferably at least one anionogenic or anionic group per molecule.

The preparation of the cosmetic compositions according to the present invention is known to the skilled person. The amount of polymer in the composition will depend on its application and can easily be determined.

A wide variety of additional components may be employed in cosmetic and personal care compositions according to the present invention. The additional components used in a particular composition will depend on kind of composition and its intended use and can therefore be selected by the skilled person. Examples of suitable additional components include:

A perfume or fragrance, for example in an amount of from 0.01% to 1% by weight of the total composition.

Sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

Anti-dandruff actives such as zinc pyrithione, piroctone olamine, selenium disulphide, sulphur, coal tar, and the like.

Hair conditioning agents such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.

Surfactants for hair shampoo and conditioner compositions. For a shampoo, the level is preferably from about 10% to about 30%, preferably from 12% to about 25%, by weight based on total weight of the composition. For conditioners, the preferred level of surfactant is from about 0.2% to about 3%, by weight based on total weight of the composition. Surfactants useful in compositions of the present invention include anionic, nonionic, cationic, zwitterionic and amphoteric surfactants.

Carboxylic acid polymer thickeners for hair shampoo and conditioner compositions. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and derived from a polyhydric alcohol. Examples of carboxylic acid polymer thickeners useful herein are those selected from the group consisting of carbomers, acrylates/C10-C30 alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners, by weight based on total weight of the composition.

Emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10. Polysorbate 80, cetyl phosphate, potassium cetyl phosphate, diethanolamine cetyl phosphate. Polysorbate 60, glyceryl stearate. PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.

Vitamins and derivatives thereof (e.g., ascorbic acid, vitamin E, tocopheryl acetate, retinoic acid, retinol, retinoids, and the like).

Cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).

And further preservatives, antioxidants, chelators and sequestrants; and aesthetic components such as for example colourings, hair nutrients and essential oils.

As solvents the compositions according to the invention may comprise water, alcohols, preferably ethanol, and dimethylether. Preferably the composition according to the invention is a hair care composition.

The invention also relates to a container comprising the composition according to the invention. The composition is brought into the market in all kind of containers, so that the consumer is able to store and use the composition. Suitable containers are for example bottles and pots, but also spray cans and siphons if for example the composition is a hair care composition.

EXAMPLE 1

Preparation of Polyoxazolidone-1

In an apparatus fitted with stirrer, dropping funnel, thermometer, reflux condenser and equipment for operating under nitrogen, 80 mmol neopentylglycol, 160 mmol dimethylol propanoic acid and 30 g methyl ethyl ketone were precharged. Next 300 mmol of isophorone diisocyanate, containing 1% LiBr.(Bu)$_3$P=O, was added dropwise at 85° C. When the reaction mixture was clear it was heated to 145° C. till refluxing methyl ethyl ketone. Then 40 mmol polytetrahydrofuran diglycidyl ether (Mn=780, Grilonit F713 of EMS) was added. After 1 hour the reaction mixture was cooled to 45° C. and 30 g acetone were added. Next the remaining isocyanate groups were deactivated by adding 16 g 2-amino-2-methylpropanol. Subsequently water was added to the reaction mixture and the reaction product was further neutralized with 2-amino-2-methylpropanol till pH about 8.0. The methyl ethyl ketone and acetone were distilled off under vacuum at 45° C. to give an aqueous solution of the polyoxazolidone polymer.

EXAMPLE 2

Preparation of Polyoxazolidone-2

In an apparatus fitted with stirrer, dropping funnel, thermometer, reflux condenser and equipment for operating under nitrogen, 50 mmol polypropylene glycol diglycidyl ether (Mn=380) and 16.7 mmol butanediol diglycidyl ether was added and the temperature was raised to 150° C. Next 50 mmol of isophorone diisocyanate containing 1% LiBr.(Bu)$_3$P=O, was added dropwise. After 10 min the temperature was decreased to 85° C. and 66.7 mmol neopentylglycol, 133.3 mmol dimethylol propanoic acid and 30 g methyl ethyl ketone were added. Next 233.3 mmol of isophorone diisocyanate was added. When the reaction mixture was clear it was heated to 145° C. till refluxing methyl ethyl ketone. After 1 hour the reaction mixture was cooled to 45° C. and 30 g acetone was added. Next the remaining isocyanate groups were deactivated by adding 16 g 2-amino-2-methylpropanol. Subsequently water was added to the reaction mixture and the reaction product was further neutralized with 2-amino-2-methylpropanol till pH about 8.0. The methyl ethyl ketone and acetone were distilled off under vacuum at 45° C. to give an aqueous solution of the polyoxazolidone polymer.

EXAMPLE 3

Preparation of Polyoxazolidone-3

In an apparatus fitted with stirrer, dropping funnel, thermometer, reflux condenser and equipment for operating under nitrogen, 300 mmol of hydrogenated diphenyl methane diisocyanate, containing 1% LiBr.(Bu)$_3$P=O, was precharged. Next 40 mmol polytetrahydrofuran diglycidyl ether (Mn=780, Grilonit F713 of EMS) was added dropwise at 150° C. After 10 min and cooling down to 90° C., 80 mmol neopentylglycol, 160 mmol dimethylol propanoic acid and 30 g methyl ethyl ketone were added. The reaction mixture was then stirred until it became clear. After 1 hour the reaction mixture was cooled to 45° C. and 30 g acetone was added. Next the remaining isocyanate groups were deactivated by adding 16 g 2-amino-2-methylpropanol. Subsequently water was added to the reaction mixture and the reaction product was further neutralized with 2-amino-2-methylpropanol till pH about 8.0. The methyl ethyl ketone and acetone were distilled off under vacuum at 45° C. to give an aqueous solution of the polyoxazolidone polymer.

An aerosol hair spray formulation with Example 4 to 6: 90% VOC was made by mixing:
10% polyoxazolidone-, -2 or -3 of example 1-3

55% ethanol
35% dimethylether

EXAMPLE 7-9

A hair spray formulation with 80% VOC was made by mixing:
5% polyoxazolidone-1, -2 or -3 of example 1-3
45% ethanol
35% dimethylether
15% water

EXAMPLE 10-12

A pump hair spray formulation with 55% VOC was made by mixing:
5% polyoxazolidone-1, -2 or -3 of example 1-3
40% ethanol
35% dimethylether
40% water

EXAMPLE 13-15

Pump hairspray formulations with 0 VOC content:
5% polyoxazolidone-1, -2 or -3 of example 1-3
90% water
Film Evaluation:

The above-mentioned hairspray formulations are applied to a glass plates and the resulting films were tested for the following four criteria:
Appearance, tackiness, smoothness and ease of washout with a surfactant solution.

All formulations comprising polyoxazolidone-1: a little hazy, non tacky, smooth and easy to wash out All formulations comprising polyoxazolidone-2: clear, non tacky, smooth and brittle and easy to wash out All formulations comprising polyoxazolidone-3: clear, non tacky, smooth and easy to wash out.

The invention claimed is:

1. A method of treating hair comprising applying to hair in need of treatment a hair care composition comprising a polymer which comprises oxazolidone groups present in the main chain of the polymer, wherein the polymer is a reaction product of a reaction mixture which comprises at least one epoxy functional compound and an excess amount of at least one isocyanate functional compound.

2. A method according to claim 1, wherein at least one epoxy functional compound a diepoxide, and wherein at least one isocyanate functional compound a diisocyante.

3. A method according to claim 1, wherein the at least one epoxy functional compound is at least one compound selected from the group consisting of epoxy terminated polyethylene glycol, epoxy terminated polypropylene glycol, epoxy terminated polytetrahydrofuran, diglycidyl ethers of ethylene glycol, diglycidyl ethers of diethylene glycol, diglycidyl ethers of neopentylglycol, and diglycidyl ethers of butane diol.

4. A method according to claim 1, wherein the at least one isocyanate functional compound is selected from tolylene-2, 4-diisocyanate, tolylene-2, 6-diisocyanate, isophorone diisocyanate, diphenyl methane diisocyanate, hydrogenated diphenyl methane diisocyanate, hexamethylene-1, 6-diisocyanate.

5. A method according to claim 1, wherein the oxazolidone group comprising polymer further comprises at least one hydroxyl functional compound and/or at least one amine functional compound.

6. A method according to claim 1, wherein the polymer is formed in a process wherein in the first step the at least one epoxy functional compound and the at least one isocyanate functional compound are reacted to form a polyoxazolidone group containing polymer precursor and wherein in one or more further steps the polymer precursor is reacted with at least one hydroxyl functional compound and/or at least one amine functional compound.

7. A method according to claim 6, wherein the at least one hydroxyl functional compound is an amino alcohol.

8. A method according to claim 6, wherein the at least one hydroxyl and/or at least one amine functional compound comprises at least one ionogenic or ionic group per molecule.

9. A method according to claim 8, wherein the at least one ionogenic or ionic group is an aniogenic or anionic group.

* * * * *